United States Patent [19]

Feldman et al.

[11] 4,419,294

[45] Dec. 6, 1983

[54] CARBODIIMIDE OLIGOMERS OF TERTIARY ALIPHATIC ISOCYANATES

[75] Inventors: Allan M. Feldman, Norwalk; Peter S. Forgione, Stamford, both of Conn.

[73] Assignee: American Cyanamid Company, Stamford, Conn.

[21] Appl. No.: 355,820

[22] Filed: Mar. 8, 1982

[51] Int. Cl.³ .......................................... C07C 119/055
[52] U.S. Cl. .......................... 260/453 A; 260/453 AR
[58] Field of Search ...................... 260/453 AR, 453 A

[56] References Cited

U.S. PATENT DOCUMENTS 4,120,884  10/1978  Woerner et al. ............ 260/453 AR
4,143,063   3/1979  Alberino et al. ............. 260/453 A

*Primary Examiner*—Dolph H. Torrence
*Attorney, Agent, or Firm*—Steven J. Hultquist

[57] ABSTRACT

Tertiary aliphatic diisocyanate carbodiimide oligomers useful in the formulation of light stable urethane spray coatings prepared by catalytic conversion of diisocyanate monomers such as tetramethylxylylene diisocyanates and dipentene diisocyanate.

9 Claims, No Drawings

CARBODIIMIDE OLIGOMERS OF TERTIARY ALIPHATIC ISOCYANATES

This invention relates to polyurethanes and in particular provides novel tertiary aliphatic diisocyanates having a polycarbodiimide functionality which are useful as intermediats and as cross-linking agents and in formulations for polyurethane spray coatings.

In the formulation of isocyanates, for example, with polyols, in spray coating applications it is desirable from a safety standpoint to minimize the vapor pressure of the isocyanate compounds utilized in the compositions. As the same time the formulation should result in a polyurethane coating characterized by light stability, hardness and resistance to heat, water and other environmental factors.

It has been known for some time that the molecular weight of diisocyanates can be increased with consequent decrease in vapor pressure by the formation of polymers having a plurality of carbodiimide linkages. The reaction proceeds quite readily at moderate temperatures splitting out $CO_2$ utilizing phospholene oxides, triaryl arsine oxides, and other catalysts, but the polymerization proceeds rapidly to solid products which are not useful in preparing spray formulations. Efforts have been made to stop the reaction of diisocyanates to form carbodiimide linked polymers by catalyst selection and by the use of chain stopping reagents.

It has now been found that carbodiimide oligomers of diisocyanates can be formed in the presence of conventional catalysts for the formation of carbodiimides from isocyanates utilizing diisocyanates in which the isocyanato group is attached to a tertiary aliphatic carbon atom. In this instance the process can be terminated at high levels of dimer and trimer, as desired, to produce stable liquid products which are uniquely desirable in the preparation of spray coating formulations by reason of the low vapor pressure of such products and their relatively high NCO content and because such products can be used to produce hard coatings characterized by thermal, hydrolytic and light stability.

Generally the products of the invention are mixtures of compounds characterized by the formula

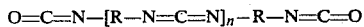

in which n is an integer from 1 to 10 and R represents a divalent hydrocarbon radical having terminal tertiary carbon such as

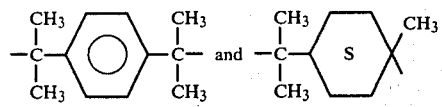

Particularly suitable monomers include the tetramethylxylylene diisocyanates and dipentenediisocyanate.

Generally, the reaction can be carried out in solvent medium although no solvent is required. The preferred solvent is toluene, although other inert solvents such as benzene, xylenes and the like can be utilized.

The catalysts are conventional for the reaction to release carbon dioxide upon heating of isocyanates. The preferred catalysts are volatile, such as phospholene oxides, e.g., 1-ethyl-3-methyl-3-phospholene-1-oxide, since these are readily distilled from the oligomer products to separate the catalyst and stop the reaction, and since the resulting products are stable. Triarylarsine oxides can also be used; however, such catalysts are much more active and generally are non-volatile making them difficult to separate and leading to unstable products. The amount of catalyst is generally that which is sufficient to produce the desired reaction and will vary typically between 0.05 and 10 parts by weight for every 100 parts of diisocyanate.

The reaction is carried out by heating the monomer in the presence of the catalyst, and solvent if any, to a temperature in the range of 25° to 250° C. Oxygen should be excluded, for example by conducting the reaction under an inert atmosphere. The amount of unreacted monomer is monitored, and reaction is terminated generally at a monomer level of 25 to 45% when the dimer is to be maximized.

When the reaction is discontinued the unreacted monomer and catalyst are removed by distillation at reduced vapor pressure, for example, in a wiped film evaporator. The recovered monomer, catalyst and solvent if any, can be recycled with fresh monomer.

EXAMPLE I

A charge of 2.050 moles of m-TMXDI ($\alpha,\alpha,\alpha',\alpha'$-tetramethyl-p-xylene-$\alpha,\alpha'$-diisocyanate) and of 0.0147 moles of 1-ethyl-3-methyl-3-phospholene-1-oxide was deaerated by sweeping with nitrogen gas for one-half hour. The mixture was then stirred under a blanket of nitrogen at 150° C. for a period of 23 hours. At that time the residual monomer content was 38.5% on a weight basis, as shown by GLC analysis. The isocyanato content was 5.33 meq/g (22.4 weight %) and the product distribution, as determined by Gel Permeation Chromotography (GPC), was 34% monomer, 34% dimer, 18% trimer, 8% tetramer and 6% higher oligomers.

The reaction mixture was run through a wiped film evaporator over a two hour period at a temperature of about 165° C. and a pressure of 4 mm Hg. Two fractions were collected. The distillate contained ⅔ of the residual monomer and catalyst. The non-volatile product was again passed through the wiped film evaporator to give a final product having less than 0.5% monomer and less than 3% catalyst which was a light yellow viscous oil having an NCO content of 3.57 meq/g (15 weight percent). The oily product consisted of 55% dimer, 27% trimer, 12% tetramer and 7% higher oligomers. It forms cross-linked polymers with different polyols that are light, heat and hydrolytically stable.

Additional m-TMXDI was added to the above distillate to provide a catalyst ratio of 0.007, and the mixture was again heated at 160° C. for 25 hours with the recovery of a product by the same technique which was similar to that obtained by the initial reaction.

EXAMPLE II

A charge of p-TMXDI was reacted in accordance with the procedure of Example I with essentially the same product distribution on work-up.

EXAMPLE III

Dipentenediisocyanate (DPDI)

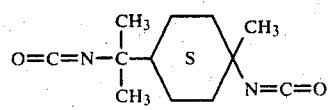

was similarly reacted as in Example I utilizing reaction times 5 to 10 times longer. The same product distributions of oligomers were obtained as in Example I after work-up in the same manner.

We claim:

1. A stable, liquid diisocyanate consisting essentially of a mixture of oligomers of the formula

wherein n is an integer from 1 to 10 and R represents a divalent hydrocarbon group having tertiary terminal carbon atoms.

2. A diisocyanate according to claim 1 in which R is

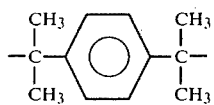

3. A diisocyanate according to claim 1 in which R is

4. A diisocyanate according to claim 1 in which R is

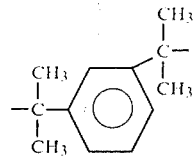

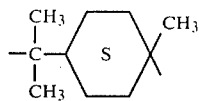

5. A method for producing diisocyanate oligomers having carbodiimide linkages which comprises polymerizing a tertiary aliphatic diisocyanate in the presence of a volatile catalyst and at a temperature effective to produce such oligomers and carbondioxide while monitoring the amount of monomer, and separating the oligomers from catalyst and unreacted monomer at a predetermined minimum level of unreacted monomer.

6. A process according to claim 5 in which the diisocyanate is a tetramethylxylylene diisocyanate.

7. A process according to claim 6 in which the diisocyanate is p-tetramethylxylylene diisocyanate.

8. A process according to claim 6 in which the diisocyanate is m-tetramethylxylylene diisocyanate.

9. A process according to claim 5 in which the diisocyanate is dipentene diisocyanate.

* * * * *